United States Patent [19]

Bertus

[11] 4,164,519
[45] Aug. 14, 1979

[54] OXIDATIVE DEHYDROGENATION PROCESSES

[75] Inventor: Brent J. Bertus, Bartlesville, Okla.

[73] Assignee: Phillips Petroleum Company, Bartlesville, Okla.

[21] Appl. No.: 616,719

[22] Filed: Sep. 25, 1975

Related U.S. Application Data

[62] Division of Ser. No. 451,476, Mar. 15, 1974, Pat. No. 3,933,933, which is a division of Ser. No. 245,382, Apr. 19, 1972, Pat. No. 3,821,324.

[51] Int. Cl.² ............................................. C07C 11/12
[52] U.S. Cl. .................................................... 585/622
[58] Field of Search .......................... 260/680 E, 683.3

[56] References Cited

U.S. PATENT DOCUMENTS

| 2,547,380 | 4/1951 | Fleck | 252/437 |
| 3,621,072 | 11/1971 | Watanabe et al. | 260/680 E |
| 3,640,900 | 2/1972 | McClellan et al. | 252/437 |

Primary Examiner—Delbert E. Gantz
Assistant Examiner—Joseph A. Boska

[57] ABSTRACT

Organic compounds, particularly hydrocarbons, are oxidatively dehydrogenated to more unsaturated compounds by contact, under reaction conditions, with air, steam and a calcined solid catalyst composition comprising titanium, at least one component selected from the group consisting of tungsten or molybdenum, and at least one component selected from the group consisting of phosphorus, bismuth, lead, antimony or arsenic. Representative of such oxidative dehydrogenation processes is the conversion of butane to butenes and butadienes.

4 Claims, No Drawings

OXIDATIVE DEHYDROGENATION PROCESSES

This is a division of copending application Ser. No. 451,476, filed Mar. 15, 1974, now U.S. Pat. No. 3,933,933, which is a division of application Ser. No. 245,382, filed Apr. 19, 1972, now U.S. Pat. No. 3,821,324.

The present invention relates to chemical processes. More particularly, the invention relates to catalytic processes for the dehydrogenation of organic compounds, particularly hydrocarbon compounds. Still more particularly, the invention relates to novel catalyst composites and their use in the catalytic dehydrogenation of organic compounds.

A widely used conversion method in the chemical processing industry is the dehydrogenation of organic compounds to compounds containing a higher degree of unsaturation, and which might be less plentiful and therefore more valuable. A number of catalytic dehydrogenation processes have been developed which have attained some measure of commercial success. Some of these are oxidative dehydrogenation processes.

The ultimate, utopian dehydrogenation process has not yet been discovered. As a consequence, it is still a continuing goal of the chemical processing industry to find alternative catalytic dehydrogenation methods. Such alternative methods become valuable on occasion because they can, depending upon the specific circumstances, provide convenience and economies that can make the difference in whether a specific chemical processing scheme is practical or not. For any given combination of starting feed material and desired product, it is desirable to have a large number of alternative catlyst systems to consider. From these a catalyst and process can be chosen which provide the most acceptable combination of results in terms of minimum side reactions, high conversion rates, high yields, and high selectivities to the desired product. Also of importance are catalysts which have a low susceptibility to deactivation, and which can be operated for long periods of time without regeneration and/or which can be readily regenerated to an activity approaching that of the freshly prepared catalysts. Each of these process aspects can vary with the specific situation.

A number of oxidative dehydrogenation systems which include halogens or halogen-releasing compounds are known in the art. Most of these include solid inorganic contact masses which give improved results apparently by promoting the oxidation of halides, thereby regenerating elemental halogen which is the primary dehydrogenation agent. Such processes exhibit many disadvantages in regard to equipment corrosion and the expense of continuously feeding, recovering and recycling and relatively expensive halogen materials. Halogen-free dehydrogenation systems remain the most desirable for use in dehydrogenation processes, particularly in oxidative dehydrogenation processes.

It is an object of this invention to provide a process for the dehydrogenation of organic compounds to compounds having a greater degree of unsaturation.

Another object of the invention is to provide a process for the dehydrogenation in the presence of oxygen of a hydrocarbon feedstock to more unsaturated compounds.

Still another object of the invention is to provide catalyst composites for use in oxidative dehydrogenation processes.

Other objects, aspects, and advantages of the invention will become apparent to those skilled in the art upon consideration of the accompanying disclosure.

Broadly speaking, according to this invention, dehydrogenatable organic compounds, particularly hydrocarbons, are oxidatively dehydrogenated to compounds having a greater degree of unsaturation by contact, under reaction conditions, with a free oxygen-containing gas, steam, and a calcined solid catalyst composition comprising titanium, at least one of the group consisting of tungsten or molybdenum, and at least one of the group consisting of phosphorus, bismuth, lead, antimony or arsenic.

The catalysts of the present invention are compositions which can be represented by the empirical formula

$$TiMe_xMe'_yO_z,$$

wherein Ti is titanium; Me represents at least one member selected from the group consisting of tungsten (W) or molybdenum (Mo); Me' represents at least one member selected from the group consisting of phosphorus (P), bismuth (Bi), lead (Pb), antimony (Sb) or arsenic (As); wherein x and y are numbers in the range of 0.01 to about 5, preferably about 0.1 to about 1, and wherein z is a number determined by the proportions and by the valence requirements of the calcined elements of the mixture, i.e., z is a fixed number representing the amount of oxygen necessary to satisfy any unsatisfied valences of the calcined metallic elements of the mixture. The elements contained in the catalysts are not necessarily present in the elemental state but can be combined with each other or with sufficient oxygen to form one or more neutral compounds such as titanium oxide, tungsten oxide, molybdenum phosphate, bismuth phosphate, lead molybdate, antimony oxide, arsenic oxide, and the like, and mixtures of these, depending upon the identity and proportions of the elements present.

These catalysts can also be supported on, or diluted with, a conventional catalytic support material such as silica, alumina, boria, magnesia, titania, zirconia, and the like, and combinations thereof, as well as with other similar conventional catalyst support materials known in the art.

Some preferred catalyst compositions can be represented by Ti/Mo/P/O, Ti/W/Bi/O, Ti/Mo/Pb/O, Ti/W/P/O, Ti/Mo/Bi/O, Ti/W/As/O, Ti/W/Sb/O, and Ti/Mo/Sb/O. Particularly effective are catalyst compositions represented by Ti/Mo/P/O, Ti/W/Bi/O, Ti/Mo/Pb/O, wherein the atomic ratios of Mo, P, W, Bi, and Pb to titanium is in the range of 0.01–5, preferably 0.1–1.

The catalysts of the present invention can be prepared by any suitable method. Conventional methods such as coprecipitation, impregnation, dry mixing, wet mixing, and combinations thereof, can be used. In general, any method can be used which will provide an intimately-mixed and calcined composition containing the above-described elements in the above-described atomic proportions and preferably having a catalytic surface of at least about 1 square meter per gram.

Substantially any titanium compound, or tungsten or molybdenum compound, or phosphorus, bismuth, lead, antimony, or arsenic compound can be employed in the preparation of these catalysts so long as none of the compounds are detrimental to the final oxidative dehydrogenation catalyst, and so long as essentially all of the elements in the compounds used, other than oxygen and the elements listed above, are removed from the final catalyst either by a prior washing step or by a volatilization such as during calcination. However, small amounts of some other elements involved in the preparation of the catalyst can be tolerated in the final catalytic composition. For example, if alkali metal or alkaline earth metal hydroxides are used in the procedure involving precipitation, small residual amounts of such alkali or alkaline earth metals are not damaging to the final catalyst composition. Similarly, if some of the elements of the catalyst are originally in the sulfate form, small residual amounts of sulfur in the final catalyst composition can also be tolerated. Halogen residues, on the other hand, are generally considered undesirable and these should be minimized.

Generally, the preferred titanium compounds, Me compounds, and Me' compounds are either oxides of these elements or compounds which are convertible to the oxide on calcination. Some examples of these are titanium oxide, ammonium metatungstate, ammonium molybdate, phosphoric acid, bismuth nitrate, lead dioxide, arsenic acid, antimony oxide, and the like, and mixtures thereof.

In one method of catalyst preparation, compounds of the desired metals can simply be mixed, in a finely divided state, in the presence of sufficient water to form a slurry or paste. The compounds need not necessarily be soluble in water. The slurry or paste is then dried, and calcined to form an intimate mixture of the ingredients. The calcined mixture can, if desired, be formed into pellets, tablets, or other suitable catalyst shapes using suitable forming methods.

In another alternative catalyst preparation method, solutions of suitable catalyst preparation compounds are coprecipitated from aqueous solutions by the addition of alkali metal, or alkaline earth metal, or ammonium hydroxides. The resulting precipitates are then filtered, washed, dried, and calcined. In another modification, two or more of such metal compounds can be coprecipitated and the resulting precipitate, either in the wet gel stage or in the calcined state, can be impregnated with a solution of another catalyst ingredient.

Still another catalyst preparation method is to boil a solution containing soluble compounds of the catalyst preparation elements until sufficient water has been removed and the mixture becomes viscous or syrupy and can then be dried and calcined. Regardless of the method used to prepare the catalyst and regardless of the specific sequence of steps used, the last stage of the preparation is generally activation by calcination in an oxygen-containing gas such as air, or air and steam, at a temperature in the range of 900° to about 1800° F. for about 0.1 to about 24 hours or until the catalyst is active for oxidative dehydrogenation.

The feedstocks which are applicable for the oxidative dehydrogenation process of the present invention comprise dehydrogenatable organic compounds having from about 2 to about 12 carbon atoms per molecule and at least one

grouping, that is, adjacent carbon atoms each being bonded to at least one hydrogen atom. Hydrocarbons have been found to be particularly suitable as feedstocks. Particularly applicable are acrylic paraffins and monoolefins, preferably having from 4 to about 12 carbon atoms. These can be branched or unbranched. Acyclic monoolefins having 4 to 12 carbon atoms are particularly responsive. Conversion of butane to butenes and butadiene, conversion of isopentane to isoamylenes and isoprene, the conversion of butenes to butadiene, and the conversion of isoamylenes to isoprene are presently considered most advantageous with the process and catalysts of the present invention. Product mono- and diolefins such as these are useful as monomers which can be polymerized to moldable resins and elastomers.

Some examples of other feeds include ethane, propane, isobutane, pentane, hexane, 2-methylhexane, octane, dodecane, 2,4-dimethyloctane, 2-methylbutene-1, hexene-2, octene-1, 3-methylnonene-4, dodecene-1, and the like, including mixtures thereof.

The dehydrogenatable feedstocks can be oxidatively converted according to the process of the present invention under any suitable conditions. In general, these conditions comprise a temperature in the range of about 800° to about 1300° F., preferably 950° to 1200° F.; a convenient pressure such as 7 to 250 psia; and a volumetric oxygen-hydrocarbon ratio of about 0.1:1 to about 4:1. The presence of added steam is generally beneficial and volumetric steam:hydrocarbon ratios of 0.1:1 to 50:1 can be used. The hydrocarbon feed rate will generally be in the range of from about 50 to about 5000 GHSV, volume of gas per volume of catalyst per hour. The fixed catalyst bed is the preferred mode of contact, but other modes such as a fluidized bed can also be used.

The dehydrogenation process is ordinarily carried out by forming a mixture, preferably a preheated mixture, of the dehydrogenatable feed, the oxygen-containing gas, and the steam, and passing this mixture over the catalyst at the desired temperature and pressure. The effluent from the reaction zone is subjected to any suitable separation method, such as fractionation, to isolate and recover the desired products. Unconverted feeds or partially converted materials can be recycled.

Generally, at least trace amounts of oxygenated byproducts are also formed in these reactions. For example, compounds such as furan, acetaldehyde, furfural, and acetic acid can be obtained. Some carbon oxides will be formed as well as some cracking products.

The catalyts of the present invention can be utilized for long periods of time without regeneration. However, when regeneration has become necessary, this can be accomplished by merely cutting off the flow of dehydrogenatable feedstock and allowing the catalyst to be contacted with the oxygen and steam for a sufficient period of time to restore activity to the catalyst.

The following examples are illustrative of the invention.

EXAMPLE I

Several invention catalysts were prepared. This was carried out by dry mixing compounds containing the desired elements, adding sufficient water to make a slurry, and drying the slurry at 300° F. followed by calcination at 1200° F. for 3 hours. The catalysts were then crushed, and screened to an 8/40 mesh. The following Table I shows the catalyst ingredients and the atomic proportions of the elements within the catalyst composition based upon the amounts of the ingredients used.

TABLE I

| Catalyst | 25 g | 20 g | 10 g | Atomic Proportions |
|---|---|---|---|---|
| Ti/Mo/P/O | $TiO_2$ | $MoO_3$ | $H_3PO_4$ (85%) | $TiMo_{0.44}P_{0.33}$ |
| Ti/W/Bi/O | $TiO_2$ | $H_2WO_4$ | $Bi(NO_3)_3 \cdot 5H_2O$ | $TiW_{0.25}Bi_{0.06}$ |
| Ti/Mo/Pb/O | $TiO_2$ | $MoO_3$ | $PbCO_3$ | $TiMo_{0.44}Pb_{0.12}$ |
| Ti/W/P/O | $TiO_2$ | $H_2WO_4$ | $H_3PO_4$ (86%) | $TiW_{0.25}P_{0.33}$ |
| Ti/Mo/Bi/O | $TiO_2$ | $MoO_3$ | $Bi(NO_3)_3 \cdot 5H_2O$ | $TiMo_{0.44}Bi_{0.06}$ |
| Ti/W/As/O | $TiO_2$ | $H_2WO_4$ | $H_3AsO_4$ | $TiW_{0.25}As_{0.22}$ |
| Ti/W/Sb/O | $TiO_2$ | $H_2WO_4$ | $Sb_2O_3$ | $TiW_{0.25}Sb_{0.21}$ |
| Ti/Mo/Sb/O | $TiO_2$ | $MoO_3$ | $Sb_2O_3$ | $TiMo_{0.44}Sb_{0.21}$ |

EXAMPLE II

Several catalysts, prepared in Example I above, were tested for activity in the oxidative dehydrogenation of isopentenes to isoprene. The catalysts were charged into fixed bed reactors and contacted with a mixture of isopentenes, air and steam at 1050° F. and at atmospheric pressure. After being on-stream for 12 hours, the effluents were sampled and analyzed by gas-liquid chromatography. The results of these runs, together with other operating conditions are shown in Table II below.

TABLE II

| | Oxidative Dehydrogenation of Isopentenes to Isoprene | | |
|---|---|---|---|
| Catalyst | Ti/Mo/P/O | Ti/W/Bi/O | Ti/Mo/Pb/O |
| Isopentenes, GHSV | 400 | 400 | 400 |
| Oxygen, GHSV | 660 | 660 | 660 |
| Steam: Isopentenes Vol. Ratio | 27.4 | 23.1 | 27.7 |
| Conversion, % | 47.7 | 60.7 | 56.9 |
| Modivity to Isoprene[1], % | 60.9 | 67.7 | 57.3 |

[1]Modivity is a modified selectivity based on the analysis of only gas phase products which include isoprene, unconverted feed, cracked products, and carbon oxides.

The data in the table above demonstrate that the catalyst of the present invention shows substantial activity for oxidative dehydrogenation of isopentenes to isoprene.

EXAMPLE III

Several catalysts prepared in Example I above were tested for the oxidative dehydrogenation of butane to butenes and/or butadiene. Each of the catalysts was charged into a fixed bed reactor and contacted with a mixture of normal butane, air and steam. The butane was passed in at 50 GHSV, oxygen at 50 GHSV and the steam:butane volumetric ratio was 10:1. After 15 minutes onstream at 900° F., the reactor effluents were sampled and analyzed by gas-liquid chromatography. The temperature was then increased to 1050° F. After 1 hour at 1050° F., the effluents were sampled and analyzed again.

The results of these tests are shown in Table III below.

TABLE III

| Oxidative Dehydrogenation of Butane to Butenes and Butadiene | | |
|---|---|---|
| | 900° F. (15 min.) | 1050° F. (1 hr.) |
| Ti/W/P/O Catalyst | | |
| Conversion, % | 0.6 | 21.3 |
| Modivity to Butenes + Butadiene, % | 50.1 | 19.2 |
| Modivity to Butadiene only, % | 0 | 7.8 |
| Ti/Mo/P/O Catalyst | | |
| Conversion, % | 15.6 | 14.6 |
| Modivity to Butenes + Butadiene, % | 0 | 9.9 |
| Modivity to Butadiene only, % | 0 | — |
| Ti/W/Bi/O Catalyst | | |
| Conversion, % | 2.0 | 7.4 |
| Modivity to Butenes + Butadiene, % | 0 | 17.5 |
| Modivity to Butadiene only, % | 0 | — |
| Ti/Mo/Bi/0 Catalyst | | |
| Conversion, % | 1.5 | 17.7 |
| Modivity to Butenes + Butadiene, % | 81.4 | 23.8 |
| Modivity to Butadiene only, % | 0 | 8.5 |
| Ti/W/As/O Catalyst | | |
| Conversion, % | 7.6 | 35.1 |
| Modivity to Butenes + Butadiene, % | 49.9 | 38.6 |
| Modivity to Butadiene only, % | 13 | — |
| Ti/W/Sb/O Catalyst | | |
| Conversion, % | 0.1 | 24 |
| Modivity to Butenes + Butadiene, % | 0 | 27.1 |
| Modivity to Butadiene only, % | 0 | 0.8 |
| Ti/Mo/Sb/O Catalyst | | |
| Conversion, % | 14.5 | 20.4 |
| Modivity to Butenes + Butadiene, % | 0 | 8.6 |
| Modivity to Butadiene only, % | 0 | 2.4 |

The data in the foregoing table demonstrate that the catalysts of the present invention also exhibit activity for the oxidative dehydrogenation of butane, although the level of activity appears lower with this paraffin and reaction temperatures somewhat higher than 900° F. are apparently required for best results.

As will be apparent to those skilled in the art from the above discussion, various modifications can be made in

What is claimed is:

1. A process for the oxidative dehydrogenation of a dehydrogenatable hydrocarbon having from 4 to 12 carbon atoms which comprises contacting said feedstock under dehydrogenation conditions in the presence of molecular oxygen with a catalyst consisting essentially of titanium, molybdenum, phosphorus and combined oxygen, said catalyst being characterized by the expression $$TiMo_xP_yO_z$$

wherein x and y are numbers in the approximate range of 0.01 to 5 and z is a number determined by the valence requirements of said titanium, molybdenum and phosphorus.

2. The process of claim 1 wherein the values of x and y are in the approximate range of 0.1 to 1.

3. The process of claim 1 wherein said feedstock is isopentene.

4. The process of claim 2 wherein said x is 0.44 and y is 0.33.

* * * * *